(12) United States Patent
Dickerson et al.

(10) Patent No.: US 11,059,771 B2
(45) Date of Patent: Jul. 13, 2021

(54) WARMING SENSATION COMPOUNDS

(71) Applicant: TAKASAGO INTERNATIONAL CORPORATION, Tokyo (JP)

(72) Inventors: Thalia S. Dickerson, Haskell, NJ (US); Louis J. Lombardo, Washingtonville, NY (US); Michael E. Lankin, High Bridge, NJ (US); Jennifer B. Tartaglia, Mahwah, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/314,920

(22) PCT Filed: Aug. 4, 2017

(86) PCT No.: PCT/US2017/045638
§ 371 (c)(1),
(2) Date: Jan. 3, 2019

(87) PCT Pub. No.: WO2018/027202
PCT Pub. Date: Feb. 8, 2018

(65) Prior Publication Data
US 2019/0169111 A1    Jun. 6, 2019

Related U.S. Application Data

(60) Provisional application No. 62/370,923, filed on Aug. 4, 2016.

(51) Int. Cl.
| | |
|---|---|
| *C07C 69/734* | (2006.01) |
| *A23G 1/32* | (2006.01) |
| *A23G 4/12* | (2006.01) |
| *A23G 4/06* | (2006.01) |
| *A23G 1/42* | (2006.01) |
| *C07C 69/732* | (2006.01) |
| *A23L 27/20* | (2016.01) |
| *A61K 8/37* | (2006.01) |
| *A61K 8/42* | (2006.01) |

(52) U.S. Cl.
CPC ............. *C07C 69/734* (2013.01); *A23G 1/32* (2013.01); *A23G 1/42* (2013.01); *A23G 4/06* (2013.01); *A23G 4/12* (2013.01); *C07C 69/732* (2013.01); *A23L 27/204* (2016.08); *A23V 2002/00* (2013.01); *A23V 2200/15* (2013.01); *A61K 8/37* (2013.01); *A61K 8/42* (2013.01)

(58) Field of Classification Search
CPC .......................... C07C 69/732; C07C 69/734
See application file for complete search history.

(56) References Cited

U.S. PATENT DOCUMENTS

| | | |
|---|---|---|
| 5,773,410 A | 6/1998 | Yamamoto |
| 8,741,958 B2 | 6/2014 | Lombardo et al. |
| 2019/0276386 A1* | 9/2019 | Backes ............... A23L 27/84 |

FOREIGN PATENT DOCUMENTS

| | | |
|---|---|---|
| CN | 102503826 B | 10/2014 |
| GB | 2 168 974 A | 7/1986 |
| WO | WO 90/15055 A1 | 12/1990 |
| WO | WO 2015/018182 A1 | 2/2015 |
| WO | WO 2015/158677 A1 | 10/2015 |
| WO | WO 2016/082780 A1 | 6/2016 |

OTHER PUBLICATIONS

Bunyak et al. "The synthesis and evaluation of 6-alkylidene-2'β-substituted penam sulfones as β-lactamase inhibitors" Bioorganic & Medicinal Chemistry Letters, vol. 9, Issue 14, pp. 1997-2002 (Year: 1999).*
Cain, "Contribution of the Trigeminal Nerve to Perceived Odor Magnitude," Annals New York Academy of Sciences 237:28-34 (1974).
Green et al., "Evaluating the 'Labeled Magnitude Scale' for Measuring Sensations of Taste and Smell," Chem. Senses 21:323-334 (1996).
International Search Report dated Nov. 13, 2017 in International Application No. PCT/US2017/045638.
Jacquot et al., "Influence of nasal trigeminal stimuli on olfactory sensitivity," C. R. Biologies 327:305-311 (2004).
LeBlanc et al., "Synthesis and Antiradical/Antioxidant Activities of Caffeic Acid Phenethyl Ester and Its Related Propionic, Acetic, and Benzoic Acid Analogues," Molecules 17:14637-14650 (2012).
Yan et al., "Identification of blapsins A and B as potent small-molecule 14-3-3 inhibitors from the insect *Blaps japanensis*," Bioorganic & Medicinal Chemistry Letters 22(12):4179-4181 (2012).
Database Registry, Registry No. 1962956-83-7, 2-phenoxyethyl 2-(4-hydroxy-3-methoxyphenyl) acetate, Entered STN: Jul. 29, 2016.
Busnena et al., "Olive secoiridoids and semisynthetic bioisostere analogues for the control of metastatic breast cancer," Bioorganic & Medicinal Chemistry, 21(7):2117-2127 (2013).
Touaibia et al., "Sinapic acid phenethyl ester as a potent selective 5-lipoxygenase inhibitor: Synthesis and structure—activity relationship," Chem Biol Drug Des, 92(5):1876-1887 (2018).

* cited by examiner

*Primary Examiner* — Joseph R Kosack
(74) *Attorney, Agent, or Firm* — Baker Botts L.L.P.

(57) ABSTRACT

Novel compounds for use in flavor, fragrance, or topical compositions are provided. Specifically, the compounds of the presently disclosed subject matter provide effective and unexpected warming sensations. The composition can be incorporated into various consumer end products, including flavors, fragrances, and topical applications.

16 Claims, No Drawings

WARMING SENSATION COMPOUNDS

CROSS-REFERENCE TO RELATED APPLICATIONS

This application is a U.S. National Stage Patent Application under 35 U.S.C. § 371 of International Application No. PCT/US2017/045638, filed on Aug. 4, 2017, which claims priority to U.S. Provisional Patent Application Ser. No. 62/370,923, filed Aug. 4, 2016, the contents of each of which are incorporated by reference herein in their entirety.

FIELD

The presently disclosed subject matter relates to compounds that impart a physiological warming or heating sensation to the skin or mucous membranes, such as those within the nose or mouth, and to flavor, fragrance and/or topical compositions comprising such warming compounds. The disclosed subject matter also relates to consumer products comprising such warming compounds and/or flavor, fragrance, or topical compositions.

BACKGROUND

There is continuing interest in flavor, fragrance, and topical compositions that can effectively stimulate the senses. There is particular interest in novel chemesthetic agents, in particular, that can stimulate or activate receptors of the nervous system that are associated with senses that mediate pain, touch and thermal perception through the skin or mucous membranes.

The trigeminal system, a part of the nervous system, includes nasal cavity surface receptors, pathways and sensory fibers which conduct from the trigeminal nerve to the brain. Through the stimulation of the trigeminal nerve endings in mucus membranes such as the nose or mouth, or in the skin, a variety of different sensations can be induced that are important in the perception of flavors and fragrances.

Trigeminal nerves, sensory nerves, and epithelial cells mediate chemesthetic, taste, and aroma sensations which can be caused by chemical activation of ion channels. Trigeminal-stimulating compounds can induce a variety of different sensations by activation of these ion channels. By way of non-limiting example, sensations induced by trigeminal-stimulating compounds can include irritation, tickling, burning, stinging, tingling, warming, cooling, and/or astringency. Transient receptor potential (TRP) channels impacted by trigeminal-stimulating compounds include TRPV (inducing a warming sensation), TRPA (inducing a tingling or irritating sensation) and TRPM (inducing a cooling sensation). Trigeminal-stimulating compounds can also be known as chemesthetic compounds or chemesthetic agents.

Substances which are capable of producing a sensation described as warming or imparting a sensation of heat are particularly useful to flavorists and perfumers and others with the ability to create new, unique flavorings and fragrances for use in a wide variety of consumer products. Thus, flavorists and perfumers are continually reliant on the development of novel compounds which can provide a warming or heating sensation to the skin or mucous membranes, such as those within the nose or mouth.

An object of the presently disclosed subject matter is to provide novel compounds and compositions containing the compounds that can effectively and unexpectedly impart a desired sensation to the senses.

SUMMARY OF THE INVENTION

The presently disclosed subject matter is related to the compound represented by Formula (I):

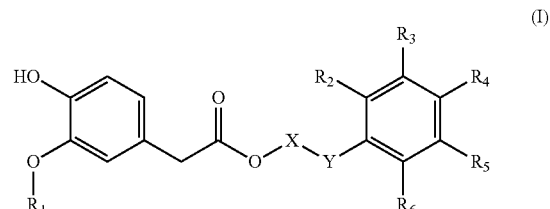

wherein
$R_1$ is a hydrogen atom, a methyl group, or an ethyl group;
$R_2$, $R_3$, $R_4$, $R_5$, and $R_6$ are each independently a hydrogen atom, a linear or branched alkyl or alkenyl group from 1 to 5 carbons, an alkoxy group, a hydroxyl group, a substituted or unsubstituted phenyl group, or where $R_3$ and $R_4$ together are selected from a group consisting of —OCH$_2$O—, —OCH$_2$CH$_2$—, —OCH$_2$CH$_2$O—, or —OCH$_2$CH$_2$CH$_2$—;
X is group containing one to five linear or branched carbon atoms;
Y is represented by an oxygen atom or a group represented by (CH$_2$)$_m$ where m is equal to 0 or 1;
provided that when:
 $R_1$ is a methyl group
 X is a group containing from two to five linear or branched carbon atoms and
 Y is a group represented by (CH$_2$)$_m$, then
 $R_2$, $R_3$, $R_4$, $R_5$, and $R_6$ are all not a hydrogen atom or a linear or branched alkyl or alkenyl group.

The presently disclosed subject matter is also related to the compound represented by Formula (II):

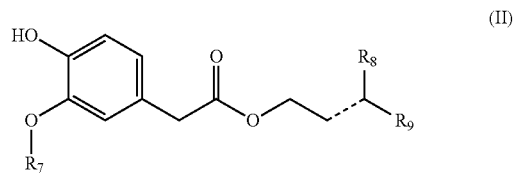

wherein
the dashed line represents a single or double bond;
$R_7$ and $R_8$ are each independently a hydrogen atom, a methyl group, or an ethyl group;
$R_9$ is a linear or branched alkyl or alkenyl group containing 4 to 12 carbon atoms, provided that when $R_8$ is a hydrogen atom that $R_9$ is not chosen from the group represented by Formula (Z)

where n is an integer from 0 to 7 and A and B are each independently a hydrogen atom, a methyl group, or an ethyl group.

The presently disclosed compounds can include, but are not limited to, compounds of Formula (I) and (II), as well as constitutional isomers, enantiomers, stereoisomers, and racemic mixtures of said compounds listed herein.

In certain embodiments, the presently disclosed subject matter is directed to warming compositions comprising one or more compounds according Formula (I) or (II).

In certain embodiments, the warming composition comprises 2-Phenoxyethyl 2-(4-hydroxy-3-methoxyphenyl)acetate, (E)-3,7-Dimethylocta-2,6-dien-1-yl 2-(4-hydroxy-3-methoxyphenyl)acetate, or mixtures thereof.

In certain embodiments, the warming composition further comprises at least one additional warming agent. In specific embodiments, the at least one warming agent is selected from the group consisting of vanillyl ethyl ether, vanillyl propyl ether, vanillin propylene glycol acetal, ethyl vanillin propylene glycol acetal, capsaicin, gingerol, vanillyl butyl ether, 4-(1-menthoxy-methyl)-2-phenyl-1,3-dioxolane, 4-(1-menthoxy-methyl)-2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3',4'-methylenedioxy-phenyl)-1,3-dioxolane, black pepper extract, cinnamaldehyde, piperine, hot pepper oil, red pepper oleoresin, *Capsicum* oleoresin, ginger oleoresin, nonyl acid vanillylamide, 4-(1-menthoxy-methyl)-2-(3'-methoxy-4'-hydroxyphenyl)-1,3-dioxolane, vanillin-1,2-hexylene glycol acetal, vanillin-1,2-butylene glycol acetal, vanillin-1-butoxyglycerol acetal, ethyl vanillin, ethyl vanillyl alcohol (3-ethoxy-4-hydroxybenzyl alcohol), ethyl homovanillate, vanillyl isopropyl ether, and all stereoisomers and mixtures thereof.

In certain embodiments, the warming compositions are formulated as a flavor, fragrance or topical composition.

The presently disclosed subject matter is also directed to flavor or fragrance compositions comprising the warming compositions comprising at least one compound according to Formula (I) or Formula (II). In certain embodiments, the flavor or fragrance composition further comprises at least one non-warming trigeminal stimulating agent. In specific embodiments, the non-warming trigeminal stimulating compound is selected from the group consisting of menthol, menthone, camphor, pulegol, isopulegol, cineole, 2-isopropyl-N-2,3-trimethylbutyramide, N-ethyl-2-isopropyl-5-methylcyclohexane carboxamide, ethyl 3-(p-menthane-3-carboxamido)acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methyl-cyclohexyl)-amide, N-[4-(2-Amino-2-oxoethyl)phenyl]-p-menthanecarboxamide, menthyl pyrrolidone carboxylate, cubebol, icilin, 1-(2-hydroxy-4-methylcyclohexyl)ethanone, N-(4-(cyanomethyl)phenyl)-2-isopropyl-5,5-dimethylcyclohexane-1-carboxamide, 2-isopropyl-5-methylcyclohexyl 4-(dimethylamino)-4-oxobutanoate, N-benzo[1,3] dioxol-5-yl-3-p-menthanecarboxamide, N-benzooxazol-4-yl-3-p-menthanecarboxamide, N-4-([1,2,4]triazol-1-yl)-phenyl-3-p-menthanecarboxamide, N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-diemethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, 6-isopropyl-9-methyl-1,4-dioxaspiro-(4,5)-decane-2-methanol, 2-[(2-p-menthoxy)ethoxy]ethanol, menthyl succinate, menthyl glutarate, dimenthyl succinate, dimenthyl glutarate, menthyl lactate, menthone glycerin ketal, mint oil, peppermint oil, spearmint oil, *Eucalyptus* oil, spilanthol, sanshool, hydroxy y-sanshool, hydroxy-sanshool, sanshool-I, sanshool II, sanshoamide, Japanese pepper extract, chavicine, *Echinacea* extract, northern prickly ash extract, Nepalese spice timur extract, 4-(1-menthoxymethyl)-2-phenyl-1,3-dioxolane, N-isobutyldeca-(2,4)-dienamide, N-cyclopropyl-(2E,6Z)-nonadienamide, N-ethyl-(2E,6Z)-nonadienamide, jambu oleoresin, allyl-isothiocyanate, 4-hydroxybenzyl isothiocyanate, mustard oil, wasabi extract, elemol, elimicin, lime oxide, elemi oil, ocimene quintoxide, 2-isopropenyl-5-methyl-5-vinyltetrahydrofuran, and all stereoisomers and mixtures thereof.

The presently disclosed subject matter is also directed to topical compositions comprising the warming compositions comprising at least one compound according to Formula (I) or Formula (II). In certain embodiments, the topical composition further comprises at least one non-warming trigeminal stimulating agent.

The presently disclosed subject matter is also directed to consumer products comprising the warming compositions disclosed herein, along with a consumer product base. In alternative embodiments, the presently disclosed subject matter is also directed to consumer products comprising a flavor or fragrance composition disclosed herein, along with a consumer product base.

The presently disclosed subject matter is also directed to methods to improve, enhance or modify the taste or odor properties of a flavor or fragrance composition by adding to said composition an effective quantity of one or more of the compounds disclosed herein.

In another aspect, the presently disclosed subject matter provides a method to modify, enhance or improve a consumer product by adding to the base of that consumer product a quantity of the compounds of Formula (I) or Formula (II) effective to produce a warming sensation after contact with the skin or mucous membrane of an individual.

The foregoing has outlined rather broadly the features and technical advantages of the present application in order that the detailed description that follows can be better understood. Additional features and advantages of the application will be described hereinafter which form the subject of the claims of the application. It should be appreciated by those skilled in the art that the conception and specific embodiment disclosed can be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

DETAILED DESCRIPTION

As discussed above, there is a continuing need in the art to identify novel compounds that effectively stimulate the trigeminal system. The presently disclosed subject matter addresses this need through the discovery of compounds that can impart a strong warming sensation.

For clarity, and not by way of limitation, the detailed description is divided into the following subsections:
1. Definitions;
2. Warming Compounds and Warming Compositions;
3. Flavor, Fragrance, and/or Topical Compositions; and
4. Use of Compositions in Consumer Products.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextrorotatory or levorotatory) which they rotate plane polarized light at the wavelength of the sodium D line. The compounds of the presently disclosed subject matter contain one or more asymmetric centers and can thus give rise to enantiomers, diastereomers, and other stereoisomeric forms that can be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers can be prepared using chiral synthons or chiral reagents, or resolved using conventional techniques. If the compound contains a double bond, the substituent can be E or Z configuration. If the compound contains a disubstituted cycloalkyl, the cycloalkyl substituent can have a cis- or trans-configuration. All tautomeric forms are also intended to be included.

As used herein, the term "isomers" refers to different compounds that have the same molecular formula but differ in arrangement and configuration of the atoms. Also as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

The term "consumer product" means products intended to be used or consumed in the form in which it is sold, and not intended for subsequent commercial manufacture or modification. Non-limited examples of consumer products are described in more detail herein.

As used herein, "fragrance" can also be used interchangeably with aroma, scent or odor.

As used herein, the term "intensity" can describe the extent or degree to which an olfactory, taste or chemesthetic stimulus can be perceived as measured by a variety of scales known to those skilled in the art, including, by way of example, the Labeled Magnitude Scale (LMS) or the Descriptive Analysis Testing for Sensory Evaluation (ASTM Manual 13). See, B. Green et al., Chem. Senses 21(3): 323-334 (1996), and ASTM International Manual Series-MNL 13—Descriptive Analysis Testing For Sensory Evaluation, R. C. Hootman, Ed. 1992 (West Conshohocken, Pa.) ISBN 0-8031-1756-6.

As used herein, the term "strength" can be used interchangeably with "intensity" in the consumer and expert sensory panelist vernacular.

As used herein, the terms "trigeminal-stimulating compounds" and "compounds that stimulate the trigeminal system" refer to compounds that can stimulate or activate the trigeminal system and, specifically, the trigeminal nerve. See, W. S. Cain, Annals New York Academy of Sciences 237:28-34 (1974). Trigeminal-stimulating compounds can impart various sensations to the mucous membranes, including the oral cavity, nasal cavity, throat, and/or skin. See, L. Jacquot et al., C. R. Biologies 327:305-311 (2004). In certain embodiments, the trigeminal-stimulating compound can be a cooling compound, a warming compound, and/or tingling compound. Two or more trigeminal-stimulating compounds can be combined.

Certain trigeminal-stimulating compounds, when used at levels below a certain threshold ("sub-threshold levels"), can stimulate the user's trigeminal system in such a way that the user perceives a sensation not specifically identifiable as irritation, tickling, burning, stinging, tingling, warming, cooling, astringency, etc. Without being bound to any particular theory, it can be that when used at sub-threshold levels in conjunction with other flavor or fragrance materials, certain trigeminal-stimulating compounds can influence the flavor or fragrance perceived by a user despite not being individually identifiable as irritating, tickling, burning, stinging, tingling, warming, cooling, or astringent agents.

Trigeminal-stimulating compounds can be naturally or synthetically derived. Both naturally derived and synthetically derived trigeminal-stimulating compounds can be used in conjunction with the presently disclosed subject matter. In certain embodiments, the trigeminal-stimulating compounds can be entirely naturally derived, entirely synthetically derived, or a mixture of naturally derived and synthetically derived compounds. In certain embodiments, the trigeminal-stimulating compounds can include racemates and isomers. In certain embodiments, the trigeminal-stimulating compounds can have an optical isomer and chemical purity of greater than 90%, preferably greater than 95%, more preferably greater than 97.5%, and even more preferably greater than 99%. Purity can be determined by gas chromatography using the method described in U.S. Pat. No. 5,773,410 by summing the area percent of impurity peaks and subtracting these from the total measured area which is taken to be 100%.

As used herein, the term "warming agent" is used to refer to compounds that can stimulate or activate the trigeminal system and, specifically, the trigeminal nerve, to induce a sensory benefit that is described as warming or heating, and the term "non-warming trigeminal-stimulating agents" refer to compounds that can stimulate or activate the trigeminal system and, specifically, the trigeminal nerve, to induce a sensory benefit that is not described as warming or heating. By way of non-limiting example, sensations induced by non-warming trigeminal-stimulating agents can include irritation, tickling, stinging, tingling, cooling, and/or astringency.

All publications, including but not limited to patents and patent application, cited in this application are herein incorporated by reference as if each individual publication were specifically and individually indicated to be incorporated by reference herein as though fully set forth.

2. Warming Compounds and Warming Compositions

The presently disclosed subject matter is directed to a compound represented by Formula (I):

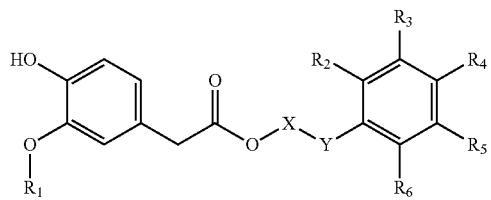

wherein $R_1$ is a hydrogen atom, a methyl group, or an ethyl group;

$R_2$, $R_3$, $R_4$, $R_5$, and $R_6$ are each independently a hydrogen atom, a linear or branched alkyl or alkenyl group from 1 to 5 carbons, an alkoxy group, a hydroxyl group, a substituted or unsubstituted phenyl group, or where $R_3$ and $R_4$ together are selected from a group consisting of —OCH$_2$O—, —OCH$_2$CH$_2$—, —OCH$_2$CH$_2$O—, or —OCH$_2$CH$_2$CH$_2$—;

X is group containing one to five linear or branched carbon atoms;

Y is represented by an oxygen atom or a group represented by (CH$_2$)$_m$ where m is equal to 0 or 1;

provided that when:

$R_1$ is a methyl group

X is a group containing from two to five linear or branched carbon atoms and

Y is a group represented by (CH$_2$)$_m$, then $R_2$, $R_3$, $R_4$, $R_5$, and $R_6$ are all not a hydrogen atom or a linear or branched alkyl or alkenyl group.

The presently disclosed subject matter is also directed to a compound represented by Formula (II):

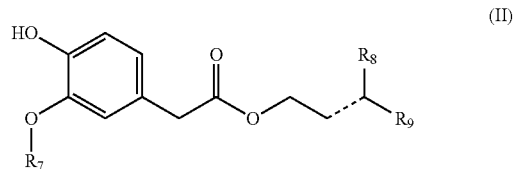

wherein
the dashed line represents a single or double bond,
$R_7$ and $R_8$ are each independently a hydrogen atom, a methyl group, or an ethyl group,
$R_9$ is a linear or branched alkyl or alkenyl group containing 4 to 12 carbon atoms, provided that when $R_8$ is a hydrogen atom that $R_9$ is not chosen from the group represented by Formula (Z)

where n is an integer from 0 to 7 and A and B are each independently a hydrogen atom, a methyl group, or an ethyl group.

The presently disclosed compounds can include, but are not limited to, compounds of Formula (I) and (II), as well as constitutional isomers, enantiomers, stereoisomers, and racemic mixtures of said compounds listed herein.

Non-limiting examples of compounds of Formulas (I) and (II) include (S)-3,7-dimethyloct-6-en-1-yl 2-(4-hydroxy-3-methoxyphenyl)acetate, 3,7-dimethyloctyl 2-(4-hydroxy-3-methoxyphenyl)acetate, (E)-3,7-dimethylocta-2,6-dien-1-yl 2-(4-hydroxy-3-methoxyphenyl)acetate, 3,7-dimethyloct-6-en-1-yl 2-(4-hydroxy-3-methoxyphenyl)acetate, (Z)-3,7-dimethylocta-2,6-dien-1-yl 2-(4-hydroxy-3-methoxyphenyl)acetate, 2-phenoxyethyl 2-(4-hydroxy-3-methoxyphenyl)acetate, 2-(p-tolyloxy)ethyl 2-(4-hydroxy-3-methoxyphenyl)acetate, 2-(4-isopropylphenoxy)ethyl 2-(4-hydroxy-3-methoxyphenyl)acetate, 2-(4-methoxyphenoxy)ethyl 2-(4-hydroxy-3-methoxyphenyl)acetate, 3-(4-methoxyphenyl)-2-methylpropyl 2-(4-hydroxy-3-methoxyphenyl)acetate, 3-(4-(tert-butyl)phenyl)-2-methylpropyl 2-(4-hydroxy-3-methoxyphenyl)acetate, 3-(4-(tert-butyl)phenyl)propyl 2-(4-hydroxy-3-methoxyphenyl)acetate, 2,2-dimethyl-3-(m-tolyl)propyl 2-(4-hydroxy-3-methoxyphenyl)acetate, and dec-9-en-1-yl 2-(4-hydroxy-3-methoxyphenyl)acetate.

Compounds of Formula (I) or Formula (II) can be prepared by methods and under conditions known to one skilled in the art. Non-limiting example methods of producing the presently described compounds are shown in Examples 1 to 14 herein. It has advantageously been found that the presently disclosed compounds can be used as a warming agent. In certain embodiments, the compounds of the presently disclosed subject matter can be used alone or in combination to comprise a warming composition. In one embodiment, the warming composition comprises 2-Phenoxyethyl 2-(4-hydroxy-3-methoxyphenyl)acetate, (E)-3,7-Dimethylocta-2,6-dien-1-yl 2-(4-hydroxy-3-methoxyphenyl)acetate, or a combination thereof.

In certain embodiments, the warming composition comprises one or more of the presently disclosed compounds and at least one additional warming agent. By way of non-limiting example, warming agents can include, but are not limited to, vanillyl ethyl ether, vanillyl propyl ether, vanillin propylene glycol acetal, ethyl vanillin propylene glycol acetal, capsaicin, gingerol, vanillyl butyl ether, 4-(1-menthoxy-methyl)-2-phenyl-1,3-dioxolane, 4-(1-menthoxy-methyl)-2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3',4'-methylenedioxy-phenyl)-1,3-dioxolane, black pepper extract, cinnamaldehyde, piperine, hot pepper oil, red pepper oleoresin, *Capsicum* oleoresin, ginger oleoresin, nonyl acid vanillylamide, 4-(1-menthoxy-methyl)-2-(3'-methoxy-4'-hydroxyphenyl)-1,3-dioxolane, vanillin-1,2-hexylene glycol acetal, vanillin-1,2-butylene glycol acetal, vanillin-1-butoxyglycerol acetal, ethyl vanillin, ethyl vanillyl alcohol (3-ethoxy-4-hydroxybenzyl alcohol), ethyl homovanillate, vanillyl isopropyl ether, and all stereoisomers and mixtures thereof. In certain embodiments, warming trigeminal-stimulating compounds can include vanillyl ethyl ether, vanillyl propyl ether, vanillyl butyl ether, vanillin, vanillyl alcohol, ethyl vanillin, ethyl vanillyl alcohol, or a mixture thereof.

In certain other embodiments, the warming composition further comprises one or more solvents or diluents. Such solvents or diluents include but are not limited to ethanol, propylene glycol, triethyl citrate, medium chain triglycerides (MCT), triacetin, or deionized or distilled water.

The compounds represented by Formula (I) and (II) above have a strong warming sensation when in contact with the skin or mucous membranes, such as those within the nose, mouth, or throat.

In one aspect of the disclosed subject matter, the compounds of Formula (I) or Formula (II) can be employed alone or in combination as a warming composition. It is advantageous and desirable to provide variations in the onset of the perception of warming and the duration of such perceptions, including without limitation, (i) providing the perception of warming immediately upon first contact of the compound to the skin or mucous membrane; (ii) providing the perception of warming after a lag time between first contact and when the warming sensation is first detected; (iii) providing a perception of warming lasting a few seconds or minutes before the perception wanes; or (iv) providing a perception of warming lasting more than a few minutes before the perception wanes. In certain embodiments the compounds of Formula (I) or Formula (II) can be employed alone or in combination to vary the onset (i.e., quick or delayed) and duration of the perceived warming sensation. Such warming compositions can be utilized in flavor or fragrance compositions for use in consumer products.

3. Flavor, Fragrance, and/or Topical Compositions

The compounds of the presently disclosed subject matter can be formulated into different flavor, fragrance, and/or topical compositions. A flavor, fragrance, and/or topical composition in accordance with the presently disclosed subject matter can include one or more, two or more, or three or more of the compounds described above.

In certain embodiments, the presently disclosed warming compositions can be utilized in flavor, fragrance, or topical compositions wherein it is desirable for the consumer to have a perception of warmth or heat.

It can be advantageous and desirable for a flavor, fragrance, and/or topical composition to (i) provide multiple sensory benefits, or (ii) to enhance the perception or duration of specific sensory benefits by combining a warming agent with one or more non-warming trigeminal stimulating agents, or (iii) in the case of fragrance compositions, to improve the hedonic experience, intensity, or noticeability of a fragrance composition in a way such that a specifically identifiable warming sensation is not perceived such as disclosed in PCT Application No. PCT/US16/019430, the contents of which are hereby incorporated by reference in their entirety.

Thus, in certain other embodiments, the flavor, fragrance, and/or topical compositions described herein further comprise one or more non-warming trigeminal stimulating agents. Such agents can include but are not limited to cooling, tingling, pungent, or irritating agents. Those skilled in the art will recognize that certain warming agents, such as by way of non-limited example, piperine and cinnamaldehyde, may also be utilized as agents to provide non-warming sensations.

By way of non-limiting example, non-warming trigeminal-stimulating agents can include, but are not limited to, menthol, menthone, camphor, pulegol, isopulegol, cineole, 2-isopropyl-N-2,3-trimethylbutyramide, N-ethyl-2-isopropyl-5-methylcyclohexane carboxamide, ethyl 3-(p-menthane-3-carboxamido)acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methyl-cyclohexyl)-amide, N-[4-(2-Amino-2-oxoethyl)phenyl]-p-menthanecarboxamide, menthyl pyrrolidone carboxylate, cubebol, icilin, 1-(2-hydroxy-4-methylcyclohexyl)ethanone, N-(4-(cyanomethyl)phenyl)-2-isopropyl-5,5-dimethylcyclohexane-1-carboxamide, 2-isopropyl-5-methylcyclohexyl 4-(dimethylamino)-4-oxobutanoate, N-benzo[1,3] dioxol-5-yl-3-p-menthanecarboxamide, N-benzooxazol-4-yl-3-p-menthanecarboxamide, N-4-([1,2,4]triazol-1-yl)-phenyl-3-p-menthanecarboxamide, N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-diemethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, 6-isopropyl-9-methyl-1,4-dioxaspiro-(4,5)-decane-2-methanol, 2-[(2-p-menthoxy)ethoxy]ethanol, menthyl succinate, menthyl glutarate, dimenthyl succinate, dimenthyl glutarate, menthyl lactate, menthone glycerin ketal, mint oil, peppermint oil, spearmint oil, *Eucalyptus* oil, spilanthol, sanshool, hydroxy γ-sanshool, hydroxy-sanshool, sanshool-I, sanshool II, sanshoamide, Japanese pepper extract, chavicine, *Echinacea* extract, northern prickly ash extract, Nepalese spice timur extract, 4-(1-menthoxymethyl)-2-phenyl-1,3-dioxolane, N-isobutyldeca-(2,4)-dienamide, N-cyclopropyl-(2E,6Z)-nonadienamide, N-ethyl-(2E,6Z)-nonadienamide, jambu oleoresin, allyl-isothiocyanate, 4-hydroxybenzyl isothiocyanate, mustard oil, wasabi extract, elemol, elimicin, lime oxide, elemi oil, ocimene quintoxide, 2-isopropenyl-5-methyl-5-vinyltetrahydrofuran, and all stereoisomers and mixtures thereof. U.S. Pat. No. 8,741,958 discloses synthesis of synthetic spilanthol, the contents of which is hereby incorporated by reference in its entirety.

In certain embodiments, non-warming trigeminal-stimulating compounds can include menthol, menthone, camphor, pulegol, isopulegol, 2-isopropyl-N-2,3-trimethylbutyramide, N-ethyl-2-isopropyl-5-methylcyclohexane carboxamide, ethyl 3-(p-menthane-3-carboxamido)acetate, 1-(2-hydroxy-4-methyl cyclohexyl)ethanone, N-(4-(cyanomethyl)phenyl)-2-isopropyl-5,5-dimethylcyclohexane-1-carboxamide, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, menthyl succinate, menthyl glutarate, dimenthyl succinate, dimenthyl glutarate, menthyl lactate, menthone glycerin ketal, mint oil, peppermint oil, spearmint oil, *Eucalyptus* oil, spilanthol, Japanese pepper extract, chavicine, *Echinacea* extract, northern prickly ash extract, Nepalese spice timur extract, 4-(1-menthoxymethyl)-2-phenyl-1, 3-dioxolane, N-isobutyldeca-(2,4)-dienamide, N-ethyl-(2E,6Z)-nonadienamide, jambu oleoresin, allyl-isothiocyanate, mustard oil, wasabi extract, elemol, elimicin, lime oxide, elemi oil, and all stereoisomers and mixtures thereof.

In certain embodiments, the presently disclosed flavor, fragrance, and/or topical compositions can further contain one or more support materials. By way of non-limiting example, support materials can include diluents (ethanol, purified water, etc.), solvents, carriers, preservatives, antioxidants, emulsifiers, resins, sugars, waxes, stabilizers, and/or other known flavor, fragrance and/or topical ingredients which are safe for use in products for consumption, inhalation and/or topical use such as those ingredients listed in reference texts such as S. Arctander, Perfume and Flavor Chemicals, 1969, Montclair, N.J., USA (or any of its more recent versions), which is herein incorporated by reference in its entirety. In certain embodiments, the flavor compositions of the present disclosure further comprise flavoring agents, antioxidants, sequestrants, emulsifiers, stabilizers, weighting agents, acids, bases, salts, sweeteners, and/or anticaking agents.

The amount of the warming compound of the present disclosure in a flavor, fragrance, and/or topical composition can vary based on the desired sensory characteristics or other properties of such flavor, fragrance, and/or topical composition.

In certain embodiments, a fragrance composition can contain one, two, three, four or more fragrance compounds. In the case of a fragrance composition, the warming compound is present in amounts of from about 0.1% to about 60% by weight, or from about 0.001% to about 50% by weight, or from about 0.01% to about 20% by weight, or from about 0.1 to about 10% by weight, or from about 0.1% to about 5% by weight, or about 0.1% to about 1% by weight based on the total weight of the composition, and values in between. In certain embodiments, one or more warming compounds can be incorporated into a fragrance composition at an amount of from about 1% to about 60%, about 5% to about 60%, about 10% to about 60%, about 20% to about 60%, or about 30% to about 60% by weight of the total fragrance composition. In certain embodiments, one or more warming compounds can be incorporated into a fragrance composition at an amount of from about 1% to about 50%, about 1% to about 40%, about 1% to about 30%, about 1% to about 20%, about 1% to about 10%, or about 1% to about 5% by weight of the total fragrance composition. In certain embodiments, one or more warming compounds can be incorporated into a fragrance composition at an amount of from about 5% to about 50%, about 5% to about 40%, or about 5% to about 30% by weight of the total fragrance composition. In certain embodiments, one or more warming compounds can be incorporated into a fragrance composition at an amount of from about 10% to about 50%, about 10% to about 40%, or about 10% to about 30% by weight of the total fragrance composition. In certain embodiments, one or more warming compounds can be incorporated into a fragrance composition at an amount of from about 20% to about 50%, about 20% to about 40%, or about 20% to about 30% by weight of the total fragrance composition. In certain embodiments, one or more warming compounds can be incorporated into a fragrance composition at an amount of from about 30% to about 50% or about 30% to about 40% by weight of the total fragrance composition. In certain embodiments, one or more warming compounds can be incorporated into a fragrance composition at an amount of about 30%, about 5% to about 15%, or about 5% to about 10% by weight of the total fragrance composition.

Non-warming trigeminal-stimulating agents and warming agents suitable for use in the fragrance compositions of the presently disclosed subject matter can have characteristic physical and/or chemical properties. By way of non-limiting example, suitable warming agents and non-warming trigeminal-stimulating agents can have characteristic molecular weights, boiling points, or vapor pressures. In certain embodiments, the warming agents or non-warming trigeminal-stimulating agents can have molecular weights of less than or no more than about 250 daltons, about 300 daltons, or about 350 daltons. In certain embodiments, the warming agents or non-warming trigeminal-stimulating compounds can have boiling points of less than or no more than about 250° C., about 300° C., or about 350° C., at atmospheric pressure. In certain embodiments, the non-warming trigeminal-stimulating compounds can have vapor pressures of less than or no more than about $1 \times 10^{-5}$ mm Hg, about $1 \times 10^{-4}$ mm Hg, or about $1 \times 10^{-3}$ mm Hg.

In certain embodiments, a flavor composition can contain one, two, three, four or more flavor compounds. In the case of a flavor composition, the warming compound is present in amounts of from about 0.0001% to about 70% by weight, or from about 0.001% to about 50% by weight, or from about 0.01% to about 30% by weight to the total weight of the composition, and values in between. In certain embodiments, the warming compound is present in amounts of from about 0.0001% to about 50% by weight, or from about 0.0001% to about 40% by weight, or from about 0.0001% to about 30% by weight, or from about 0.0001% to about 20% by weight, or from about 0.0001% to about 10% by weight, or from about 0.0001% to about 5% by weight, or from about 0.0001% to about 1% by weight based on the total weight of the composition. In certain embodiments, the warming compound is present in amounts of from about 0.0001% to about 50% by weight, or from about 1% to about 50% by weight, or from about 5% to about 50% by weight, or from about 10% to about 50% by weight, or from about 20% to about 50% by weight, or from about 30% to about 50% by weight, or from about 40% to about 50% by weight based on the total weight of the composition.

One embodiment of the presently disclosed subject matter provides a method to improve, enhance or modify the taste or odor properties of a flavor, fragrance, and/or topical composition by adding to said composition an effective quantity of one or more of the compounds of Formula (I) or Formula (II).

As used herein, the term "effective quantity" means the amount of said compounds in a flavor or frag flavor, fragrance, and/or topical composition in which the compounds will contribute characteristic warming sensation to the taste or olfactory or skin sensing properties. The compound embodied in the presently disclosed subject matter can be employed to modify the characteristics of an existing flavor, fragrance, and/or topical composition via their own sensory benefit or through affecting the sensory perception or other properties present within the said existing composition. The effective quantity will vary widely depending on the other ingredients present, their relative amounts, and the desired effect. A person of ordinary skill in the art can optimize the taste of the flavor composition, the olfactory effect of the fragrance composition, or effect on skin of the topical composition based on the incorporation of a compound of the presently disclosed subject matter. As used herein, the term "improving" is understood to mean raising a flavor, fragrance, and/or topical composition to a more desirable character, the term "enhancing" is understood to mean making the flavor, fragrance, and/or topical composition greater in effectiveness, such as strength, and the term "modifying" is understood to mean providing the flavor, fragrance, and/or topical composition with a change in character.

4. Use of Compositions in Consumer Products

The warming compositions or flavor compositions of the presently disclosed subject matter as described above can be advantageously used to impart a warming sensation to a wide variety of consumer products intended to be eaten, imbibed or otherwise tasted. Examples of such consumer products include food products, e.g., baked goods, cakes, cookies, sauces, soups, snack food, bread, dips, seasonings, salad dressings; confectionary products, e.g., chewing gum, hard candies, soft candies, chewy candies, gummy candies, chocolates; beverage products, e.g., alcoholic beverages, non-alcoholic beverages, carbonated beverages, sports drinks, flavored waters, coffee, tea, juice, fruit drinks, dairy drinks; and oral care products, e.g., toothpaste, mouthwashes, mouth rinses, film strips, breath mints; oral pharmaceuticals, e.g., throat lozenges, vitamins, chewables, nebulizers, medicinal drops. Additional examples of food products or categories include, but are not limited to, breakfast cereals, cheeses, condiments and relishes, confectionery and frostings, egg products, fats and oils, fish products, frozen dairy, fruit ices, gelatins and puddings, granulated sugar, gravies, imitation dairy products, instant coffees and teas, jams and jellies, meat products, milk products, nut products, grain products, poultry, processed fruits, processed vegetables, reconstituted vegetables, seasonings and flavors, snack foods, soups, sugar substitutes, savory sauces, and sweet sauces. These lists of products are given by way of illustration and are not to be regarded as being in any way limiting.

As noted above, a confectionary product can be chewing gum. Chewing gum base components are components known to those of ordinary skill in the art and used to provide typical chewing gum properties and include elastomers (e.g., polyisobutylene, polybutylene, isobutylene-isoprene co-polymers, styrene-butadiene co-polymers, polyvinylacetate, natural rubber, jelutong, lechi caspi, perillo); elastomer plasticizers (e.g., glycerol ester of partially hydrogenated rosin, glycerol esters of tall oil rosin, methyl and partially hydrogenated methyl esters of rosin); waxes (e.g., polyethylene, bees wax, carnauba, paraffin); fats, oils, emulsifiers, fillers (e.g., calcium carbonate, magnesium carbonate, aluminum hydroxide, magnesium and aluminum silicates, clay, alumina, cellulose polymers); texturizers (e.g., hydrogenated and partially hydrogenated vegetable oils, glycerol monostearate, cocoa butter, palmitic acid, oleic acid, linolenic acid); and optionally, sweeteners.

The warming compositions or fragrance compositions of the presently disclosed subject matter as described above can be utilized in a wide variety of consumer products intended to perfume human or animal skin or hair, paper (fragranced paper), air in a room, fabric, furnishings, dishes, hard surfaces and related materials. Examples of such consumer products include fine fragrance, e.g., eau de perfume, eau de toilette, cologne; household products, e.g. hard surface cleaners, dishwasher detergent; fabric care, e.g., softener, bleach, detergent; personal care products, e.g., shampoo, shower gel; air care products, e.g., candles, air freshener sprays, plug-in oils, wax melts; and cosmetics, e.g., moisturizing cream. This list of products is given by way of illustration and is not to be regarded as being in any way limiting.

The warming compositions or fragrance compositions of the presently disclosed subject matter as described above can also be utilized in consumer products specifically intended to provide a warming sensation to human or animal skin or mucous membranes, such as topical creams or ointments to treat pain or discomfort or induce relaxation, e.g., sports rubs, massage oils; insect repellency products, e.g., bug sprays or lotions; personal care products, e.g., cleansing lotions, soaps, shaving foam or shaving gel, depilatories, bubble bath, shampoo, dandruff treatments, deodorants or antiperspirants, cosmetics and skin care products, e.g., masks and scrubs, self-tanners, tanning accelerators, foundation, lipstick, lip gloss, skin conditioning creams, lotions or gels, lotions, moisturizers, anti-aging creams, lotion, and gels; and sexual health products, e.g., personal lubricants, condoms, massage oils. This list of products is given by way of illustration and is not to be regarded as being in any way limiting.

In certain embodiments where consumer products are intended to provide a warming sensation to human or animal skin or mucous membranes, the compounds of Formula (I) or Formula (II) are present in the consumer product in amounts up to about 10%, or in amounts up to about 5%, or in amounts up to about 3%, or in amounts up to about 1.0%, or in amounts up to about 0.5%, or in amounts up to about 0.1% by weight of the consumer product.

In certain embodiments, the compounds are utilized in topical pharmaceutical products. The term "topical pharmaceutical products" as used herein further means topical pharmaceutical compositions that transdermally deliver an active pharmaceutical ingredient. As used herein "transdermal delivery" means the administration of the active pharmaceutical by application of a cream, lotion, ointment, gel, foam, powder, tape, paste, jellies, aerosols, or spray or a cutaneous patch, e.g., decongestant rubs, nasal sprays, nicotine patches to the skin of a subject. In certain embodiments, the compounds of Formula (I), Formula (II) or Formula (II) are present in a topical pharmaceutical composition in amounts up to about 15% or in amounts up to about 10%, or in amounts up to about 5%, or in amounts up to about 3%, or in amounts up to about 1.0%, or in amounts up to about 0.5%, or in amounts up to about 0.1% by weight of the topical pharmaceutical product.

In certain embodiments where consumer products are intended to be eaten, imbibed, or otherwise tasted, the compounds of Formula (I) or Formula (II) are present in the consumer product in amounts up to about 1.5%, or in amounts up to about 1.0%, or in amounts up to about 0.5%, or in amounts up to about 0.1%, or in amounts up to about 0.01% by weight of the consumer product. In certain embodiments where consumer products are intended to be eaten, imbibed, or otherwise tasted, the compounds of Formula (I) or Formula (II) are present in the consumer product in an amount of from about 0.000001% to about 1.5%, or from about 0.000001% to about 1.0%, or from about 0.000001% to about 0.5%, or from about 0.001% to about 0.01% by weight of the consumer product. In certain embodiments, the compounds are present in the consumer product in an amount of from about 0.001% to about 1%, or from about 0.1% to about 0.5%, or from about 0.1% to about 0.3% by weight of the consumer product.

In certain embodiments, where the consumer product is a food product, the compounds of Formula (I) or Formula (II) are present in the consumer product in an amount of from about 0.0005% to about 0.001%, or from about 0.0005% to about 0.0015% by weight of the consumer product. In certain embodiments, the compounds of Formula (I) or Formula (II) are present in the consumer product in an amount of from about 0.001% to about 0.002%, or from about 0.001% to about 0.003% by weight of the consumer product. In certain embodiments, the compounds of Formula (I) or Formula (II) are present in the consumer product in an amount of from about 0.0015% to about 0.005%, from about 0.002% to about 0.005%, from about 0.0025% to about 0.005%, or from about 0.003% to about 0.006% by weight of the consumer product. In certain embodiments, the compounds of Formula (I) or Formula (II) are present in the consumer product in an amount of from about 0.0035% to about 0.01%, or from about 0.005% to about 0.01%, or from about 0.005% to about 0.02% by weight of the consumer product. In certain embodiments, the compounds of Formula (I) or Formula (II) are present in the consumer product in an amount of from about 0.0075% to about 0.015%, or from about 0.0075% to about 0.05%, or from about 0.01% to about 0.02%, or from about 0.01% to about 0.025%, or from about 0.01% to about 0.03% by weight of the consumer product. In certain embodiments, the compounds of Formula (I) or Formula (II) are present in the consumer product in an amount of from about 0.2% to about 0.5% by weight of the consumer product.

In certain embodiments, where the consumer product is a food product, such as but not limited to salsa or cheese dip, the compounds of Formula (I) or Formula (II) are present in the consumer product in an amount of from about 0.0005% to about 0.001% by weight of the consumer product. In other embodiments, the compounds of Formula (I) or Formula (II) are present in the consumer product in an amount of from about 0.005% to about 0.01% by weight of the consumer product.

In certain embodiments, where the food product is a chewing gum, the compounds of Formula (I) or Formula (II) are present in an amount of from about 0.1% to about 0.5%, or from about 0.1% to about 0.3%, or from about 0.2 to about 0.3% by weight of the consumer product.

In certain embodiments where consumer products are intended to provide fragrance, the compounds of Formula (I) or Formula (II) are present in the consumer product in an amount up to about 10%, or up to about 5.0%, or up to about 1% by weight of the consumer product. In certain embodiments where consumer products are intended to provide fragrance, the compounds of Formula (I) or Formula (II) are present in the consumer product in an amount of about 0.000001% to about 10% or about 0.001% to about 5% by weight of the consumer product. Consumer products for fragrance include those consumer products intended to perfume human or animal skin or hair, or intended to perfume paper (fragranced paper), air in a room, fabric, furnishings, dishes, hard surfaces and related materials or intended to provide a warming sensation to human or animal skin or mucous membranes.

The disclosed subject matter further provides a consumer product comprising: (a) a flavor, fragrance, and/or topical composition comprising at least one compound of Formula (I) or Formula (II); and (b) a consumer product base. The disclosed subject matter also provides a method for improving, enhancing or modifying a consumer product base by means of the addition thereto of an amount of at least one compound of Formula (I) or Formula (II) effective to provide a warming sensation when in contact with the skin or a mucous membrane, such as the nose or mouth.

The compounds described herein can be employed in a consumer product base simply by directly mixing at least one compound of Formula (I) or Formula (II), or a flavor, fragrance, and/or topical composition comprising at least one compound of Formula (I) or Formula (II), with the appropriate consumer product base. Alternatively, the compounds described herein can, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they can be chemically bonded to substrates, which are adapted to release the compound upon application of an external stimulus such as light, enzyme, or the like, and then mixed with the consumer product base. Thus, the disclosed subject matter additionally provides a method of manufacturing a consumer product, comprising the incorporation of at least one compound of Formula (I) or Formula (II), as a flavor or fragrance ingredient, either by directly admixing the compound to the consumer product base or by admixing a flavor, fragrance, and/or topical composition comprising at least one compound of Formula (I) or Formula (II), which can then be mixed with a consumer product base, using conventional techniques and methods. Through the addition of an amount of at least one compound of the presently disclosed subject matter as hereinabove described in an amount effective to impart a warming sensation, the sensory, flavor or odor notes of a consumer product base will be improved, enhanced or modified. The onset of the warming sensation, its intensity and its longevity are all influenced by the rate of penetration of the compositions through the epidermis or mucous membrane, the formulation of the warming composition and/or the consumer product base, and other factors. Useful concentrations of the warming compounds within the ranges set forth herein will vary by intended use and desired consumer perception but are ascertainable by those skilled in the art of formulating flavorings, fragrances, and/or consumer products.

In a further embodiment of the presently disclosed subject matter, a method of imparting a warming sensation to an individual comprising exposing the skin or mucous membranes, such as those in the individual's nose or mouth, of the individual to a consumer product comprising at least one compound of Formula (I) or Formula (II), or a flavor, fragrance, and/or topical composition comprising at least one compound of Formula (I) or Formula (II), is also disclosed.

EXAMPLES

The presently disclosed subject matter will be better understood by reference to the following Examples, which are provided as exemplary of the disclosed subject matter, and not by way of limitation. Abbreviations have the usual meaning in the art.

Example 1

Synthesis of 2-Phenoxyethyl 2-(4-hydroxy-3-methoxyphenyl)acetate

The present Example provides a synthesis of 2-Phenoxyethyl 2-(4-hydroxy-3-methoxyphenyl)acetate.

1.82 g (10 mmol) of 2-(4-hydroxy-3-methoxyphenyl) acetic acid and 50 ml of toluene were added to a one neck, round bottom flask, equipped with a Dean-Stark trap and condenser. While this suspension was stirred at room temperature, 1.38 g (10 mmol) of 2-phenoxyethanol was added followed by 0.10 g (1 mmol) of concentrated sulfuric acid. The mixture was then refluxed for 2 hours and the water formed was collected in the trap. The reaction mixture was then cooled to room temperature, diluted with ethyl acetate, and quenched with saturated $NaHCO_3$. Once the phases were separated, the organic phase was washed once more with saturated $NaHCO_3$ and brine. The organic layer was then dried over $MgSO_4$, filtered, and concentrated under reduced pressure. The crude product was first isolated by automated silica gel chromatography (Biotage SP1, 12-100% ethyl acetate/hexane) and finally purified via Kugelrohr distillation (100° C.-120° C.@0.45 Torr) to afford 2.33 g (77.3%) of 2-phenoxyethyl 2-(4-hydroxy-3-methoxyphenyl)acetate, which crystallized to an off-white solid (mp 56° C.).

$^1$H NMR (400 MHz, CDCl3) δ ppm 3.58 (s, 2H) 3.82 (s, 3H) 4.16 (m, 2H) 4.44 (m, 2H) 5.57 (s, 1H) 6.83 (m, 5H) 6.97 (m, 1H) 7.27 (m, 2H). $^{13}$C NMR (101 MHz, CDCl$_3$) δ ppm 40.87, 55.93, 63.30, 65.92, 111.79, 114.44, 114.70, 121.31, 122.25, 125.61, 129.62, 144.87, 146.55, 158.53, 171.96.

Example 2

Synthesis of 2-(4-methoxyphenoxy)ethyl 2-(4-hydroxy-3-methoxyphenyl)acetate

The same procedure shown in Example 1 was followed to synthesize 2-(4-methoxyphenoxy)ethyl 2-(4-hydroxy-3-methoxyphenyl)acetate using 2-(4-methoxyphenoxy)ethan-1-ol as a substrate. The yield for this reaction was 42.0%.

$^1$H NMR (400 MHz, CDCl$_3$) δ ppm 3.57 (s, 2H) 3.76 (s, 3H) 3.82 (s, 3H) 4.11 (m, 2H) 4.40 (m, 2H) 5.54 (s, 1H) 6.80 (m, 7H). $^{13}$C NMR (101 MHz, CDCl$_3$) δ ppm 40.88, 55.80, 55.95, 63.40, 66.84, 122.25, 125.63, 144.87, 146.56, 152.68, 154.28, 171.95.

Example 3

Synthesis of 2-(p-tolyloxy)ethyl 2-(4-hydroxy-3-methoxyphenyl)acetate

The same procedure shown in Example 1 was followed to synthesize 2-(p-tolyloxy)ethyl 2-(4-hydroxy-3-methoxyphenyl)acetate using 2-(p-tolyloxy)ethan-1-ol as a substrate. The yield for this reaction was 41.9%.

$^1$H NMR (400 MHz, CDCl$_3$) δ ppm 2.28 (s, 3H) 3.58 (s, 2H) 3.82 (s, 3H) 4.13 (m, 2H) 4.42 (m, 2H) 5.56 (s, 1H) 6.77 (m, 4H) 6.84 (m, 1H) 7.07 (d, 2H). $^{13}$C NMR (101 MHz, CDCl$_3$) δ ppm 20.55, 40.87, 55.95, 63.36, 66.15, 111.80, 114.42, 114.62, 122.25, 125.63, 130.04, 130.58, 144.86, 171.95.

Example 4

Synthesis of 2-(4-isopropylphenoxy)ethyl 2-(4-hydroxy-3-methoxyphenyl)acetate

The same procedure shown in Example 1 was followed to synthesize 2-(4-isopropylphenoxy)ethyl 2-(4-hydroxy-3-methoxyphenyl)acetate using 2-(4-isopropylphenoxy)ethan-1-ol as a substrate. The yield for this reaction was 49.3%

$^1$H NMR (400 MHz, CDCl$_3$) δ ppm 1.21 (d, 6H) 2.85 (m, 1H) 3.57 (s, 2H) 3.82 (s, 3H) 4.14 (m, 2H) 4.42 (m, 2H) 5.55 (s, 1H) 6.79 (m, 5H) 7.13 (m, 2H). $^{13}$C NMR (101 MHz, CDCl$_3$) δ ppm 24.27, 33.37, 40.88, 55.94, 63.37, 66.10, 122.26, 141.78, 144.87, 146.55, 156.61, 171.95.

Example 5

Synthesis of 3-(4-methoxyphenyl)-2-methylpropyl 2-(4-hydroxy-3-methoxyphenyl)acetate The same procedure shown in Example 1 was followed to synthesize 3-(4-methoxyphenyl)-2-methylpropyl 2-(4-hydroxy-3-methoxyphenyl)acetate using 3-(4-methoxyphenyl)-2-methylpropan-1-ol as a substrate. The yield for this reaction was 76.8%.

$^1$H NMR (400 MHz, CDCl$_3$) δ ppm 0.86 (d, 3H) 2.01 (m, 1H) 2.34 (dd, 1H) 2.58 (dd, 1H) 3.53 (s, 2H) 3.77 (s, 3H) 3.89 (m, 5H) 5.58 (br. s., 1H) 6.79 (m, 4H) 6.86 (m, 1H) 6.97 (m, 2H). $^{13}$C NMR (101 MHz, CDCl$_3$) δ ppm 16.66, 34.79, 38.81, 41.23, 55.32, 55.97, 68.94, 111.80, 113.76, 114.45, 122.26, 126.02, 130.08, 131.96, 144.84, 146.56, 157.98, 172.01.

Example 6

Synthesis of 3-(4-(tert-butyl)phenyl)-2-methylpropyl 2-(4-hydroxy-3-methoxyphenyl)acetate The same procedure shown in Example 1 was followed to synthesize 3-(4-(tert-butyl)phenyl)-2-methylpropyl 2-(4-hydroxy-3-methoxyphenyl)acetate using 3-(4-(tert-butyl)phenyl)-2-methylpropan-1-ol as a substrate. The yield for this reaction was 52.8%.

$^1$H NMR (400 MHz, CDCl$_3$) δ ppm 0.88 (d, 3H) 1.29 (s, 8H) 2.06 (m, 1H) 2.38 (dd, 1H) 2.60 (dd, 1H) 3.53 (s, 2H) 3.91 (m, 5H) 6.79 (m, 1H) 6.85 (m, 1H) 7.00 (d, 2H) 7.26 (d, 2H). $^{13}$C NMR (101 MHz, CDCl$_3$) δ ppm 16.84, 31.47, 34.43, 34.61, 39.25, 41.22, 55.98, 69.05, 76.79, 77.10, 77.42, 111.80, 114.44, 122.27, 125.23, 126.03, 128.83, 136.84, 144.83, 146.54, 148.88, 172.03.

Example 7

Synthesis of 3-(4-(tert-butyl)phenyl)propyl 2-(4-hydroxy-3-methoxyphenyl)acetate The same procedure shown in Example 1 was followed to synthesize 3-(4-(tert-butyl)phenyl)propyl 2-(4-hydroxy-3- methoxyphenyl)acetate using 3-(4-(tert-butyl)phenyl)propan-1-ol as a substrate. The yield for this reaction was 38.6%.

¹H NMR (400 MHz, CDCl₃) δ ppm 1.29 (s, 10H) 1.93 (m, 2H) 2.59 (d, 2H) 3.53 (s, 2H) 3.87 (s, 3H) 4.08 (m, 2H) 6.80 (m, 2H) 6.86 (m, 1H) 7.05 (d, 2H) 7.29 (d, 2H). ¹³C NMR (101 MHz, CDCl₃) δ ppm 30.19, 31.58, 34.44, 41.17, 55.99, 64.32, 111.79, 114.45, 122.23, 125.39, 126.00, 128.12, 138.09, 144.84, 146.56, 148.91, 172.04.

Example 8

Synthesis of 2,2-dimethyl-3-(m-tolyl)propyl 2-(4-hydroxy-3-methoxyphenyl)acetate The same procedure shown in Example 1 was followed to synthesize 2,2-dimethyl-3-(m-tolyl)propyl 2-(4-hydroxy-3-methoxyphenyl)acetate using 2,2-dimethyl-3-(m-tolyl)propan-1-ol as a substrate. The yield for this reaction was 48.9%.

¹H NMR (400 MHz, CDCl₃) δ ppm 0.85 (s, 5H) 2.27 (s, 2H) 2.47 (s, 2H) 3.59 (s, 2H) 3.75 (s, 2H) 3.87 (s, 2H) 5.57 (s, 1H) 6.83 (m, 4H) 6.99 (d, 1H) 7.10 (t, 1H). ¹³C NMR (101 MHz, CDCl₃) δ ppm 21.47, 24.41, 35.06, 41.45, 44.88, 55.98, 71.88, 111.85, 114.48, 122.34, 126.07, 126.90, 127.81, 131.31, 137.44, 137.98, 144.85, 146.56, 171.89.

Example 9

Synthesis of 3,7-dimethyloct-6-en-1-yl 2-(4-hydroxy-3-methoxyphenyl)acetate

The same procedure shown in Example 1 was followed to synthesize 3,7-dimethyloct-6-en-1-yl 2-(4-hydroxy-3-methoxyphenyl)acetate using 3,7-dimethyloct-6-en-1-ol as a substrate. The yield for this reaction was 35.4%.

¹H NMR (400 MHz, CDCl₃) δ ppm 0.87 (m, 4H) 1.14 (d, 1H) 1.29 (m, 1H) 1.44 (m, 3H) 1.63 (m, 9H) 1.95 (m, 3H) 3.51 (s, 3H) 3.87 (s, 4H) 4.10 (m, 3H) 5.05 (m, 1H) 5.53 (s, 1H) 6.74 (m, 1H) 6.79 (d, 1H) 6.84 (d, 1H). ¹³C NMR (101 MHz, CDCl₃) δ ppm 17.72, 19.46, 25.46, 25.79, 29.58, 35.48, 37.04, 41.17, 55.95, 63.51, 76.78, 77.09, 77.41, 111.76, 114.40, 122.20, 124.61, 126.01, 131.44, 144.79, 146.51, 172.08.

Example 10

Synthesis of 3,7-dimethyloctyl 2-(4-hydroxy-3-methoxyphenyl)acetate

The same procedure shown in Example 1 was followed to synthesize 3,7-dimethyloctyl 2-(4-hydroxy-3-methoxyphenyl)acetate using 3,7-dimethyloctan-1-ol as a substrate. The yield for this reaction was 21.8%.

¹H NMR (400 MHz, CDCl₃) δ ppm 0.85 (m, 10H) 1.16 (m, 6H) 1.45 (m, 3H) 1.62 (m, 1H) 3.51 (s, 2H) 3.86 (s, 3H) 4.10 (m, 2H) 6.74 (m, 1H) 6.81 (m, 2H). ¹³C NMR (101 MHz, CDCl₃) δ ppm 19.56, 22.77, 24.69, 28.02, 29.90, 35.57, 37.18, 39.26, 41.19, 55.95, 63.56, 111.77, 114.40, 122.19, 126.02, 144.79, 146.51, 172.10.

Example 11

Synthesis of (S)-3,7-dimethyloct-6-en-1-yl 2-(4-hydroxy-3-methoxyphenyl)acetate

The same procedure shown in Example 1 was followed to synthesize (S)-3,7-dimethyloct-6-en-1-yl 2-(4-hydroxy-3-methoxyphenyl)acetate using (S)-3,7-dimethyloct-6-en-1-ol as a substrate. The yield for this reaction was 21.4%.

¹H NMR (400 MHz, CDCl₃) δ ppm 0.87 (m, 3H) 1.15 (m, 1H) 1.29 (dd, 1H) 1.45 (m, 2H) 1.64 (m, 7H) 1.95 (m, 2H) 3.51 (s, 2H) 3.86 (s, 3H) 4.10 (m, 2H) 5.05 (m, 1H) 5.54 (s, 1H) 6.78 (m, 3H). ¹³C NMR (101 MHz, CDCl₃) δ ppm 17.72, 19.46, 25.46, 25.79, 29.58, 35.47, 37.04, 41.17, 55.95, 63.52, 111.78, 114.42, 122.19, 124.61, 126.00, 131.43, 144.80, 146.53, 172.11.

Example 12

Synthesis of dec-9-en-1-yl 2-(4-hydroxy-3-methoxyphenyl)acetate

The same procedure shown in Example 1 was followed to synthesize dec-9-en-1-yl 2-(4-hydroxy-3-methoxyphenyl)acetate using dec-9-en-1-ol as a substrate. The yield for this reaction was 23.3%.

¹H NMR (400 MHz, CDCl₃) δ ppm 1.31 (m, 9H) 1.661 (m, 4H) 1.94 (d, 1H) 2.01 (m, 1H) 3.52 (s, 2H) 3.86 (s, 3H) 4.06 (t, 2H) 4.95 (m, 1H) 5.57 (s, 1H) 5.79 (ddt, 1H) 6.75 (m, 1H) 6.79 (d, 1H) 6.84 (m, 1H).

Example 13

Synthesis of (E)-3,7-Dimethylocta-2,6-dien-1-yl 2-(4-hydroxy-3-methoxyphenyl)acetate This Example provides a synthesis of (E)-3,7-Dimethylocta-2,6-dien-1-yl 2-(4-hydroxy-3-methoxyphenyl)acetate.

1.82 g (10 mmol) 2-(4-hydroxy-3-methoxyphenyl) acetic acid and 5 mL of anhydrous dimethyl formamide were added to a two neck, round bottom flask, equipped with a nitrogen gas inlet. The resulting amber solution was stirred under nitrogen and cooled to 0° C. in an ice bath. When the desired temperature was reached, 2.06 g (10 mmol) of N,N'-dicyclohexylcarbodiimide was added to the solution followed by 0.12 g (1 mmol) of 4-dimethylaminopyridine. This suspension was stirred for 30 minutes before a solution of 1.54 g (10 mmol) (E)-3,7-dimethylocta-2,6-dien-1-ol in 50 mL of anhydrous dichloromethane was added drop-wise over a period of 30 minutes. This mixture was allowed to warm to room temperature and stirred for an additional 24 hours. The mixture was then filtered through a pad of Celite® filter aid and the pad was then washed 3 times with an additional 10 mL of fresh dichloromethane. The combined filtrate was then concentrated under reduced pressure. The crude product was first isolated by automated silica gel chromatography (Biotage SP1, 10-80% ethyl acetate/hexane) and finally purified via Kugelrohr distillation to afford 1.00 g (31.3%) of (E)-3,7-Dimethylocta-2,6-dien-1-yl 2-(4-hydroxy-3-methoxyphenyl)acetate as a colorless oil.

¹H NMR (400 MHz, CDCl3) δ ppm 1.58 (m, 4H) 1.67 (s, 6H) 2.05 (m, 4H) 3.53 (s, 2H) 3.86 (s, 3H) 4.59 (d, 2H) 5.06 (m, 1H) 5.32 (m, 1H) 5.54 (s, 1H) 6.75 (m, 1H) 6.80 (d, 1H) 6.84 (m, 1H). ¹³C NMR (101 MHz, CDCl₃) δ ppm 16.57, 17.77, 25.76, 26.37, 39.60, 41.06, 55.95, 61.88, 111.80, 114.40, 118.23, 122.21, 123.78, 125.98, 131.94, 142.52, 144.79, 146.51, 172.03.

Example 14

Synthesis of (Z)-3,7-dimethylocta-2,6-dien-1-yl 2-(4-hydroxy-3-methoxyphenyl)acetate The same procedure shown in Example 13 was followed to synthesize (Z)-3,7-dimethylocta-2,6-dien-1-yl 2-(4-hydroxy-3-methoxyphenyl)acetate using (Z)-3,7-dimethylocta-2,6-dien-1-ol as a substrate. The yield was 11.3%.

$^1$H NMR (400 MHz, CDCl$_3$) δ ppm 1.56 (m, 3H) 1.66 (s, 2H) 1.74 (s, 2H) 2.07 (m, 3H) 3.52 (m, 1H) 3.86 (s, 2H) 4.56 (d, 2H) 5.06 (t, 1H) 5.33 (m, 1H) 5.52 (s, 1H) 6.74 (m, 1H) 6.79 (d, 1H) 6.84 (m, 1H). $^{13}$C NMR (101 MHz, CDCl$_3$) δ ppm 17.73, 23.61, 25.77, 26.73, 32.26, 41.05, 55.95, 61.60, 111.79, 114.40, 119.12, 122.22, 123.62, 125.95, 132.27, 142.36, 142.84, 144.79, 146.51, 172.02.

Example 15

Perceived Warming Sensations for Oral Composition

The present Example provides the perceived warming sensation of various compounds of the presently disclosed subject matter.

A warming composition was prepared by adding 1% by weight of the warming agent of Example 1 to ethanol. The resulting warming composition was diluted at 10 ppm in water. The diluted warming composition was evaluated for its perceived warming sensations in the mouth by 5 expert evaluators following a "swish and spit" protocol, in which the sample is placed into a small tasting cup, taken into the mouth, and swished around, then the sample is spit back into the original tasting cup and disposed of. Results are shown in Table 1 below.

TABLE 1

| Participant | Comments |
| --- | --- |
| 1 | Approximately 10 seconds for onset of heat; sensation on surface of tongue and roof of mouth |
| 2 | Very quick onset of heating perception; burning like jalapeno; strong |
| 3 | Instant warming at roof of mouth, dissipates then spreads, becomes hot |
| 4 | Immediate burn, intense but fades really quickly |
| 5 | Instant onset of heat; strong, prickly burn on tongue; minimal linger, sensation is very short lived. |

Additional compounds were evaluated and compared for perceived warming sensations in the mouth by expert evaluators following the "swish and spit" protocol. The results are provided in Table 2.

TABLE 2

| Compound | # of Panelists | Concentration (ppm) | Comments |
| --- | --- | --- | --- |
| (S)-3,7-dimethyloct-6-en-1-yl 2-(4-hydroxy-3-methoxyphenyl)acetate | 8 | 20 | strong burn with delayed onset; peppery burn on tip of tongue |
| 3,7-dimethyloctyl 2-(4-hydroxy-3-methoxyphenyl)acetate | 7 | 20 | bitter; irritating in back of throat; delayed, mild heat burn; nothing on tongue |
| (E)-3,7-dimethylocta-2,6-dien-1-yl 2-(4-hydroxy-3-methoxyphenyl)acetate | 7 | 20 | late onset burning, irritation in throat; heat localized on tongue; numbing |
| 3,7-dimethyloct-6-en-1-yl 2-(4-hydroxy-3-methoxyphenyl)acetate | 5 | 40 | Slight delay of heat; strong peppery burn on tip of tongue and back of throat |
| 3-(4-methoxyphenyl)-2-methylpropyl 2-(4-hydroxy-3-methoxyphenyl)acetate | 6 | 20 | immediate onset (~1 sec onset), strong capsaicin; hot & peppery, like black pepper; strong burn on tongue and throat |
| (Z)-3,7-dimethylocta-2,6-dien-1-yl 2-(4-hydroxy-3-methoxyphenyl)acetate | 6 | 20 | delayed warming sensation, fairly strong black pepper heat; building heat on the tip of the tongue; slight floral taste; soothing, salivating |
| 3-(4-(tert-butyl)phenyl)-2-methylpropyl 2-(4-hydroxy-3-methoxyphenyl)acetate | 6 | 20 | slight warming in the back of throat; unpleasant; warming slightly builds |
| 3-(4-(tert-butyl)phenyl)propyl 2-(4-hydroxy-3-methoxyphenyl)acetate | 6 | 20 | quick onset of warming and builds quickly; mouth-watering, strong peppery effect localize on the tongue and throat |
| dec-9-en-1-yl 2-(4-hydroxy-3-methoxyphenyl)acetate | 6 | 20 | metallic, slight warming in back of throat, tingling, irritation; musty |

Example 16

Perceived Warming Sensation Versus Vanillyl Butyl Ether

A warming composition of the presently disclosed subject matter was prepared was prepared and diluted according to Example 15. A second warming composition was prepared by adding 1% by weight of vanillyl butyl ether to ethanol and diluted at 10 ppm in water. The two diluted warming compositions were evaluated and compared for perceived warming sensations in the mouth by 2 expert evaluators following a "swish and spit" protocol as described in Example 15.

Both evaluators perceived the warming sensation of the presently disclosed subject matter imparted a quicker onset of a warming sensation (described as "hot, quick on tip of tongue") than the vanillyl butyl ether composition.

Example 17

Chocolate Composition

Different compounds of the presently disclosed subject matter can provide a range of warming sensations. Depending on the need of a target sensation, different compounds can be used to meet a desired sensation. This Example provides an evaluation of the warming materials of the presently disclosed subject matter in milk chocolate.

Three test compounds (A, B, and C respectively) and *Capsicum* oleoresin (1,000,000 Scoville Heat Units, ASTA Method 21) were prepared as a 5% cut in medium chain triglycerides (MCT) and set up at 0.3% in milk chocolate. A control sample was also prepared without any warming compound. The test compounds were as follows:

A: compound of Example 5

B: compound of Example 13

C: compound of Example 1

The samples were blind coded and evaluated by 10 expert panelists. Panelists were asked to rate the warming intensity from 1 to 9 (1=none, 9=very strong), as well as to choose slow, medium or fast for onset intensity. The panelist was then asked to describe the sensation and character of each sample. The results are provided below in Table 3.

TABLE 3

|  | A | B | C |
|---|---|---|---|
| Average Warming Intensity (1-9) | 2.25 | 2.7 | 6.8 |
| Onset | Slow | Slow | Fast |
| Character/ Comments | Minimal warming sensation, doesn't last, delayed heat | Slight sensation, warming in back of throat, mild heat | Immediate heat, strong intensity, spicy character, clean, pleasant linger |

As shown in Table 3, each of the compounds exhibits a different warming intensity profile. A control sample, where no warming compound was used, had an average warming intensity of 1.7, with no to slow heat, and no heat character. Where a slower onset is desired, compound A can be used as appropriate in a product. Where slightly more sensation is desired, compound B can be used as appropriate. Where a fast and immediate onset and high warming intensity is desired, compound C can be an appropriate selection.

*Capsicum* oleoresin had an average warming intensity of 7.05, with a medium to fast onset, and corresponding comments of "heat builds, full mouth warming, lingers, irritating burn". In comparison to compound C, similar profiles are noted, however, compound C had a pleasant linger, without an irritating burn.

As used herein, "fast onset" relates to the onset of warming sensation in less than about 10 seconds (i.e., quick), and "slow onset" relates to the onset of warming sensation occurring after about 15 seconds (i.e., delayed).

Example 18

Mouth Rinse

A non-alcohol mouth rinse containing 0.003% of 2-phenoxyethyl 2-(4-hydroxy-3-methoxyphenyl)acetate was prepared using a mouthwash base and tasted by an expert panel after storage for 4 weeks, both at room temperature and at 50° C.

5 panelists swished with 20 mL of sample for 30 seconds with sensory results as recorded in Table 4.

TABLE 4

| Storage Conditions | # Panelists | Concentration (ppm) | Comments |
|---|---|---|---|
| 4 weeks at Room Temperature | 5 | 30 | Quick onset whole mouth burning sensation. |
| 4 weeks at 50° C. | 5 | 30 | Slightly milder burning sensation. |

Example 19

Salsa and Cheese Dip

The compound of Example 1 ("Compound A") was evaluated in an off-shelf salsa product (Tostito brand Mild Chunky Salsa) purchased locally.

TABLE 5

| Sample | Salsa | 1% Compound A in EtOH | Compound A level in product (ppm) |
|---|---|---|---|
| Control | 100.00% | 0.00% | 0 ppm |
| Experimental Sample 1 | 99.95% | 0.05% | 5 ppm (0.0005%) |
| Experimental Sample 2 | 99.90% | 0.10% | 10 ppm (0.001%) |
| Experimental Sample 3 | 99.75% | 0.25% | 25 ppm (0.0025%) |
| Experimental Sample 4 | 99.50% | 0.50% | 50 ppm (0.005%) |

A "swish and spit" evaluation was conducted by 5 expert panelists. All experimental samples were found to have significantly more heat than the control. The optimal range for 2-Phenoxyethyl 2-(4-hydroxy-3-methoxyphenyl) acetate in salsa was determined to be 5-10 ppm (0.0005%-0.001%).

Compound A was also evaluated in an off-shelf cheese dip product (Tostito brand Smooth & Cheesy Dip) purchased locally.

TABLE 6

| Sample | Cheese dip | 5% Compound A in MCT | Compound A level in product (ppm) |
|---|---|---|---|
| Control | 100.00% | 0.00% | 0 ppm |
| Experimental Sample 1 | 99.94% | 0.06% | 30 ppm (0.003%) |
| Experimental Sample 2 | 99.90% | 0.10% | 50 ppm (0.005%) |
| Experimental Sample 3 | 99.80% | 0.20% | 100 ppm (0.01%) |
| Experimental Sample 4 | 99.60% | 0.40% | 200 ppm (0.02%) |

A "swish and spit" evaluation was conducted by 5 expert panelists. All experimental samples were found to have significantly more heat than the control. The optimal range for 2-Phenoxyethyl 2-(4-hydroxy-3-methoxyphenyl) acetate in cheese dip was determined to be 50-100 ppm (0.005%-0.01%).

Example 20

Warming Sensation in Lotion

All materials were made with 0.5% loading of active compound in an in-house lotion base except the control, which contains no active material. There were a total of 5 panelists to evaluate the lotion samples. Table 7 provides the overall warming intensity data and comments from the panelists.

TABLE 7

| | Overall warming intensity (1 = no effect, 5 = extremely warming) | Comments |
|---|---|---|
| Control | 1.25 | No sensation; slow onset with little warming |
| (E)-3,7-dimethylocta-2,6-dien-1-yl 2-(4-hydroxy-3-methoxyphenyl)acetate | 2.70 | Slow to medium onset of heat (10-30 minutes); warm sensation last about 30 minutes; prickly, itchy irritation |
| 2-phenoxyethyl 2-(4-hydroxy-3-methoxyphenyl)acetate | 2.90 | Quick onset (<5 minutes of application); lasts about 10-20 minutes; strong warming intensity; soothing, no irritation |
| 3-(4-methoxyphenyl)-2-methylpropyl 2-(4-hydroxy-3-methoxyphenyl)acetate | 1.80 | Slow to medium onset; weak, last < 20 minutes; slight itchiness |

For 2-phenoxyethyl 2-(4-hydroxy-3-methoxyphenyl)acetate, an evaluator notice when working out (sweating), the heat sensation came back at the same intensity as first described at initial application.

Example 21

Chewing Gum Composition

A chewing gum composition comprising a warming composition of the presently disclosed subject matter was prepared.

A warming composition containing 8% of 2-Phenoxyethyl 2-(4-hydroxy-3-methoxyphenyl) acetate and three additional warming agents was prepared and formulated with a chai spice flavoring to provide a flavored chewing gum composition. The formulation of the chewing gum composition is shown in Table 2.

TABLE 2

| Component | % By Weight |
|---|---|
| Chewing Gum Base Components | 97.09 |
| Chai Flavoring | 2.43 |
| Warming Composition (containing 8% of 2-Phenoxyethyl 2-(4-hydroxy-3-methoxyphenyl) acetate) | 0.48 |

"Chewing Gum Base Components" are components known to those of ordinary skill in the art and used to provide typical chewing gum properties and include elastomers (e.g., polyisobutylene, polybutylene, isobutylene-isoprene co-polymers, styrene-butadiene co-polymers, polyvinylacetate, natural rubber, jelutong, lechi caspi, perillo); elastomer plasticizers (e.g., glycerol ester of partially hydrogenated rosin, glycerol esters of tall oil rosin, methyl and partially hydrogenated methyl esters of rosin); waxes (e.g., polyethylene, bees wax, carnauba, paraffin); fats, oils, emulsifiers, fillers (e.g., calcium carbonate, magnesium carbonate, aluminum hydroxide, magnesium and aluminum silicates, clay, alumina, cellulose polymers); texturizers (e.g., hydrogenated and partially hydrogenated vegetable oils, glycerol monostearate, cocoa butter, palmitic acid, oleic acid, linolenic acid); and optionally, sweeteners.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

From the foregoing description, various modifications and changes in the compositions and methods will occur to those skilled in the art. All such modifications coming within the scope of the appended claims are intended to be included therein.

Patents, patent applications publications product descriptions, and protocols are cited throughout this application the disclosures of which are incorporated herein by reference in their entireties for all purposes.

What is claimed is:
1. A compound represented by Formula (I):

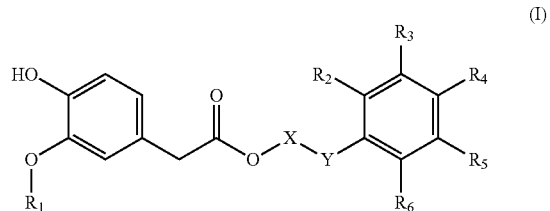

wherein
$R_1$ is a methyl group or an ethyl group;
$R_2$, $R_3$, $R_4$, $R_5$, and $R_6$ are each independently a hydrogen atom, a linear or branched alkyl or alkenyl group from 1 to 5 carbons, an alkoxy group, a hydroxyl group, a substituted or unsubstituted phenyl group, or where $R_3$ and $R_4$ together are selected from a group consisting of —OCH$_2$O—, —OCH$_2$CH$_2$—, —OCH$_2$CH$_2$O—, or —OCH$_2$CH$_2$CH$_2$—;
X is a group containing one to five linear or branched carbon atoms;
Y is represented by an oxygen atom or a group represented by (CH$_2$)$_m$ where m is equal to 0 or 1;
provided that when:
$R_1$ is a methyl group or an ethyl group,
X is a group containing from one to five linear or branched carbon atoms, and
Y is a group represented by (CH$_2$)$_m$, then
$R_2$, $R_3$, $R_4$, $R_5$, and $R_6$ are not a hydrogen atom or a linear or branched alkyl or alkenyl group.

2. A warming composition comprising one or more compounds of claim 1.

3. The warming composition of claim 2, wherein the warming composition comprises 2-Phenoxyethyl 2-(4-hydroxy-3-methoxyphenyl)acetate.

4. The warming composition of claim 2, further comprising at least one additional warming agent.

5. The warming composition of claim 4, wherein the at least one additional warming agent is selected from the group consisting of vanillyl ethyl ether, vanillyl propyl ether, vanillin propylene glycol acetal, ethyl vanillin propylene glycol acetal, capsaicin, gingerol, vanillyl butyl ether, 4-(1-menthoxy-methyl)-2-phenyl-1,3-dioxolane, 4-(1-menthoxymethyl)2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3',4'-methylenedioxy-phenyl)-1,3-dioxolane, black pepper extract, cinnamaldehyde, piperine, hot pepper oil, red pepper oleoresin, Capsicum oleoresin, ginger oleoresin, nonyl acid vanillylamide, 4-(1-menthoxy-methyl)-2-(3'-methoxy-4'-hydroxyphenyl)-1,3-dioxolane, vanillin-1,2-hexylene glycol acetal, vanillin-1,2-butylene glycol acetal, vanillin-1-butoxyglycerol acetal, ethyl vanillin, ethyl vanillyl alcohol (3-ethoxy-4-hydroxybenzyl alcohol), ethyl homovanillate, vanillyl isopropyl ether, and all stereoisomers and mixtures thereof.

6. A flavor or fragrance composition comprising the warming composition of claim 2.

7. The flavor or fragrance composition of claim 6, further comprising at least one non-warming trigeminal stimulating agent.

8. The flavor or fragrance composition of claim 7, wherein the non-warming trigeminal stimulating compound is selected from the group consisting of menthol, menthone, camphor, pulegol, isopulegol, cineole, 2-isopropyl-N-2,3-trimethylbutyramide, N-ethyl-2-isopropyl-5-methylcyclohexane carboxamide, ethyl 3-(p-menthane-3-carboxamido) acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methyl-cyclohexyl)-amide, N-[4-(2-Amino-2-oxoethyl)phenyl]-p-menthanecarboxamide, menthyl pyrrolidone carboxylate, cubebol, icilin, 1-(2-hydroxy-4-methylcyclohexyl)ethanone, N-(4-(cyanomethyl)phenyl)-2-isopropyl-5,5-dimethylcyclohexane-1-carboxamide, 2-isopropyl-5-methylcyclohexyl 4-(dimethylamino)-4-oxobutanoate, N-benzo[1,3] dioxol-5-yl-3-p-menthanecarboxamide, N-benzooxazol-4-yl-3-p-menthanecarboxamide, N-4-([1,2,4]triazol-1-yl)-phenyl-3-p-menthanecarboxamide, N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-diemethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, 6-isopropyl-9-methyl-1,4-dioxaspiro-(4,5)-decane-2-methanol, 2-[(2-p-menthoxy)ethoxy]ethanol, menthyl succinate, menthyl glutarate, dimethyl succinate, dimethyl glutarate, menthyl lactate, menthone glycerin ketal, mint oil, peppermint oil, spearmint oil, Eucalyptus oil, spilanthol, sanshool, hydroxy γ-sanshool, hydroxy-sanshool, sanshool-I, sanshool II, sanshoamide, Japanese pepper extract, chavicine, Echinacea extract, northern prickly ash extract, Nepalese spice timur extract, 4-(1-menthoxymethyl)-2-phenyl-1,3-dioxolane, N-isobutyldeca-(2,4)-dienamide, N-cyclopropyl-(2E,6Z)-nonadienamide, N-ethyl-(2E,6Z)-nonadienamide, jambu oleoresin, allyl-isothiocyanate, 4-hydroxybenzyl isothiocyanate, mustard oil, wasabi extract, elemol, elimicin, lime oxide, elemi oil, ocimene quintoxide, 2-isopropenyl-5-methyl-5-vinyltetrahydrofuran, and all stereoisomers and mixtures thereof.

9. The flavor or fragrance composition of claim 8, wherein the non-warming trigeminal stimulating compound is selected from the group consisting of menthol, menthone, camphor, pulegol, isopulegol, 2-isopropyl-N-2,3-trimethylbutyramide, N-ethyl-2-isopropyl-5-methylcyclohexane carboxamide, ethyl 3-(p-menthane-3-carboxamido)acetate, 1-(2-hydroxy-4-methylcyclohexyl)ethanone, N-(4-(cyanomethyl)phenyl)-2-isopropyl-5,5-dimethylcyclohexane-1-carboxamide, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, menthyl succinate, menthyl glutarate, dimethyl succinate, dimethyl glutarate, menthyl lactate, menthone glycerin ketal, mint oil, peppermint oil, spearmint oil, Eucalyptus oil, spilanthol, Japanese pepper extract, chavicine, Echinacea extract, northern prickly ash extract, Nepalese spice timur extract, 4-(1-menthoxymethyl)-2-phenyl-1, 3-dioxolane, N-isobutyldeca-(2,4)-dienamide, N-ethyl-(2E,6Z)-nonadienamide, jambu oleoresin, allyl-isothiocyanate, mustard oil, wasabi extract, elemol, elimicin, lime oxide, elemi oil, and all stereoisomers and mixtures thereof.

10. A topical composition comprising the warming composition of claim 2.

11. The topical composition of claim 10, further comprising at least one non-warming trigeminal stimulating agent.

12. A consumer product comprising: (a) the warming composition of claim 2; and (b) a consumer product base.

13. A consumer product comprising: (a) at least one flavor or fragrance composition of claim 6; and (b) a consumer product base.

14. A method to improve, enhance or modify the taste or odor properties of a flavor or fragrance composition by adding to the composition an effective quantity of one or more of the compounds of claim 1.

15. The method of claim 14, wherein the compound of Formula (I) is effective to produce a warming sensation after contact with the skin or mucous membrane of an individual.

16. The compound of claim 1, wherein:
$R_1$ is a methyl group or an ethyl group;
$R_2$, $R_3$, $R_4$, $R_5$, and $R_6$ are each independently selected from a hydrogen atom, a linear or branched alkyl or alkenyl group from 1 to 5 carbons, an alkoxy group, a hydroxyl group, a substituted or unsubstituted phenyl group, or where $R_3$ and $R_4$ together are selected from the group consisting of —OCH$_2$O—, —OCH$_2$CH$_2$—, —OCH$_2$CH$_2$O—, or —OCH$_2$CH$_2$CH$_2$—;
X is a group containing one to five linear or branched carbon atoms; and
Y is represented by an oxygen atom.

* * * * *